United States Patent [19]
Chandler

[11] Patent Number: 6,046,807
[45] Date of Patent: Apr. 4, 2000

[54] DIODE LASER BASED MEASUREMENT APPARATUS

[75] Inventor: Van S. Chandler, Austin, Tex.

[73] Assignee: Luminex Corporation, Austin, Tex.

[21] Appl. No.: 09/311,742

[22] Filed: May 14, 1999

Related U.S. Application Data

[60] Provisional application No. 60/085,522, May 14, 1998.
[51] Int. Cl.[7] .................................................. G01N 21/64
[52] U.S. Cl. .......................... 356/318; 356/73; 356/417; 250/458.1; 250/461.2
[58] Field of Search ............................... 356/72, 73, 317, 356/318, 417; 250/458.1, 459.1, 461.1, 461.2

[56] References Cited

U.S. PATENT DOCUMENTS

| | | | |
|---|---|---|---|
| 4,284,412 | 8/1981 | Hansen et al. | 23/230 B |
| 4,596,464 | 6/1986 | Hoffman et al. | 356/336 |
| 4,732,479 | 3/1988 | Tanaka et al. | 356/336 |
| 4,877,966 | 10/1989 | Tomei et al. | 250/458.1 |
| 5,133,602 | 7/1992 | Batchelder et al. | 356/375 |
| 5,747,349 | 5/1998 | va den Engh et al. | 436/172 |
| 5,822,067 | 10/1998 | Yanik | 356/368 |

*Primary Examiner*—F. L. Evans
*Attorney, Agent, or Firm*—Gilberto M. Villacorta; Suresh Koshy; Pepper Hamilton LLP

[57] ABSTRACT

The instant diagnostic system includes a measurement device including a laser diode and communicatable with a computer. The diagnostic system further includes a memory medium readable by the computer and storing computer instructions executable by the computer. The instructions include the following sequential, non-sequential, or independent steps. A template relating to a beam profile of the laser diode along a flow path of the measurement device is built. A fluorescent sample is captured by the measurement device. The sample is time-wise aligned to the template. The sample is normalized relative to the template. The normalized sample is integrated to determine a total amount of fluorescence in the sample.

29 Claims, 11 Drawing Sheets

DIODE LASER BASED MEASUREMENT APPARATUS

RELATED APPLICATIONS

This application claims priority to U.S. Provisional Patent Application Ser. No. 60/085,522, filed May 14, 1998 and incorporated herein by reference.

FIELD OF THE INVENTION

The present invention pertains generally to a measurement apparatus including a diode laser. More particularly, the instant invention relates to a measurement apparatus including a diode laser oriented to provide an improved beam profile.

BACKGROUND OF THE INVENTION

In vitro diagnostic assays have been performed with microspheres for over twenty years. The microspheres include microparticles, beads, polystyrene beads, microbeads, latex particles, latex beads, fluorescent beads, fluorescent particles, colored particles and colored beads. The microspheres serve as vehicles for molecular reactions. Microspheres for use in flow cytometry are obtained from manufacturers, such as Luminex Corp. of Austin, Tex.

Illustrative microspheres and methods of manufacturing same are, for example, found in U.S. patent application Ser. No. 09/234,841 to Mark B. Chandler and Don J. Chandler, entitled Microparticles with Multiple Fluorescent Signals, and in U.S. patent application Ser. No. 09/172,174 to Don J. Chandler, Van S. Chandler, and Beth Lambert, entitled Precision Fluorescently Dyed Particles and Methods of Making and Using Same, both patent applications incorporated herein by reference in their entirety. By way of example, if a user were performing an Ig G, A, M Isotyping Assay, the user opts for bead sets, such as Luminex 8070 IgG, 8060 IgA, and 8050 IgM bead sets.

Microspheres or beads range in diameter from 10 nanometers to 100 microns and are uniform and highly spherical. Bead-based assays are embodied in a standard "strip test," where beads coated with a capture reactant are fixed to a location on a paper strip and beads with another reactant occupy another position on the same paper strip. When a target analyte is introduced to the strip, the first bead type attaches to it and flows or mixes with the second, often causing a color change which indicates the presence of the target analyte.

More recent bead-based assays use flow cytometry to measure reactions with target analytes of interest. In conventional flow cytometers, as shown in FIG. 1, sample biological fluid containing sample cells or microspheres having reactants on their surfaces is introduced from a sample tube into the center of a stream of sheath fluid. The sample fluid stream is injected into, at, or near, the center of the flow cell or cuvette 1910. This process, known as hydrodynamic focusing, allows the cells to be delivered reproducibly to the center of the measuring point. Typically, the cells or microspheres are in suspension in the flow cell.

A laser diode 1900 focuses a laser beam on them as they pass through the laser beam by a flow of a stream of the suspension. Laser diodes in conventional flow cytometers often require shaping a round beam into an elliptical beam to be focused on the flow cell 1910. As shown in FIG. 1, this elliptical beam is often formed from the round beam using beam shaping optics 1960 located between the laser diode 1900 and the flow cell 1910.

When an object of interest in the flow stream is struck by the laser beam, certain signals are picked up by detectors. These signals include forward light scatter intensity and side light scatter intensity. In the flow cytometers, as shown in FIG. 1, light scatter detectors 1930, 1932 are located opposite the laser diode 1900, relative to the flow cell 1910, to measure forward light scatter intensity, and to one side of the laser, aligned with the fluid-flow/laser beam intersection to measure side scatter light intensity. Forward light scatter intensity provides information concerning the size of individual cells, whereas side light scatter intensity provides information regarding the relative size and refractive property of individual cells.

Known flow cytometers, such as disclosed in U.S. Pat. No. 4,284,412 to HANSEN et al., incorporated herein by reference, have been used, for example, to automatically identify subclasses of blood cells. The identification was based on antigenic determinants on the cell surface which react to antibodies which fluoresce. The sample is illuminated by a focused coherent light and forward light scatter, right angle light scatter, and fluorescence are detected and used to identify the cells.

As described in U.S. Pat. No. 5,747,349 to VAN DEN ENGH et al., incorporated herein by reference, some flow cytometers use fluorescent microspheres, which are beads impregnated with a fluorescent dye. Surfaces of the microspheres are coated with a tag that is attracted to a receptor on a cell, an antigen, an antibody, or the like in the sample fluid. So, the microspheres, having fluorescent dyes, bind specifically to cellular constituents. Often two or more dyes are used simultaneously, each dye being responsible for detecting a specific condition.

Typically, the dye is excited by the laser beam from a laser diode 1900, and then emits light at a longer wavelength. FIG. 1 depicts a prior art flow cytometer which uses beam splitters 1942, 1944, 1946 to direct light from the flow cell 1910 to photo-multiplier and filter sets 1956, 1958, 1959 and to side light scatter detector 1932. This flow cytometer employs a mirror 1970 to reflect forward light scatter to forward light scatter detector 1930.

In a standard flow cytometric competitive inhibition assay, by way of example, an antibody is covalently bound to microspheres. These beads are mixed with a biological sample along with a fluorescenated antigen. In the presence of an antigen of interest, the fluorescenated antigen competes for space on the beads, while in its absence, the fluorescenated antigen envelops the bead. Upon examination by flow cytometry, the presence of the antigen of interest is indicated by a marked decrease in fluorescence emission relative to a sample which contains the antigen of interest.

I have determined that there is, however, a stark contrast between these two types of bead-based assays. The former is simple and inexpensive, but is limited to crude assays with strong sample concentrations of the analyte of interest. The latter is powerful and highly sensitive, but requires a $100,000 instrument and a highly trained technician to run the assay and interpret the results.

I have recognized that there is no commercially available instrument that bridges the gap between these two types of bead-based assays. I have determined that an apparatus that combines the sensitivity and flexibility of flow cytometric assays with the simplicity and low cost of strip assays would advance the art of in vitro diagnostics.

I have recognized that much of the cost and size of a flow cytometer is attributable to the laser. Virtually all commercial flow cytometers use an argon ion 488 nm laser as an excitation source. It is large, occupying several cubic feet, requires a massive power supply, and needs constant forced air cooling to maintain stability. There are other smaller and less expensive lasers, but I have ascertained that they are unsuitable for flow cytometry. For example, dye lasers burn out too quickly. He-Cd lasers are too noisy. Frequency doubled lasers are too weak. The He-Ne laser is reasonably effective, but its red output is not the color of choice in flow cytometry.

In view of the shortcomings of the above-mentioned lasers, I have assessed the merits of laser diodes. However, I have determined that the problem with diode lasers is their beam profiles. FIG. 2a, by way of example, shows a sample beam profile of a standard laser diode. The beam profile of the laser diode is very uneven as compared to that of a standard argon ion laser, as shown, by way of example, in FIG. 2b.

I have recognized that the unevenness presents a significant obstacle for flow analyzers because associated fluorescence measurements depend upon substantially uniform excitation among particles and cells. This obstacle can be explained with reference to FIG. 3, which shows, by way of example, a two-dimensional graph of a major axis of the laser diode beam profile depicted in FIG. 2a. I have determined that if the major axis of the beam profile of FIG. 3 lies across a flow path of a flow analyzer, objects in the flow stream, such as cells or microspheres are not subject to light having the same or substantially the same energy levels. Rather, as shown in FIG. 3, points 10, 12, 14, 16, and 18 on the graph have energy levels that vary indiscriminately across the beam profile.

I have determined that if a microsphere is passing through the flow stream and subject to the laser diode beam at, for example, point 10 on the graph of the beam profile would get much more energy than, if the same microsphere were passing through the flow stream and subject to the laser diode beam at point 14. As such, I have recognized that it is impossible to distinguish between a microsphere having a high fluorescence intensity passing through a point on the beam profile having a low energy level or a microsphere having a low fluorescence intensity passing through a point on the beam profile having a high fluorescence intensity.

Commercial flow cytometers, that offer diode lasers as a second laser to accompany the argon ion laser, take for granted the large coefficients of variation (CVs) of the beam profile of the diode laser. Moreover, laser diodes need not have identical beam profiles. Indeed, even minor differences in resonating cavities, for example, affect the shape of respective beam profiles. Thus, a diode laser in a flow cytometer of a given model need not have the same beam profile of a diode laser in another flow cytometer of the same model.

As such, commercial flow cytometers, as shown by way of example, in FIG. 1, employ beam shaping optics, such as prismatic expanders, beam shaping expanders, and micro lens arrays. Prior art implementations of diode lasers in flow cytometry have attempted to optically correct the beam, steering the two outside peaks toward the center.

I have determined that such optics are unnecessarily expensive by themselves, and add to the manufacturing complexity of the flow cytometers, which, in turn, further adds to the overall cost of the instrument. Moreover, I have determined that despite the expensive and complex beam shaping optics employed, the resulting beam profile is still unsatisfactory, as shown in FIG. 4. Although the beam profile in FIG. 4 is better than that shown in FIG. 2a, for example, it still yields a ten to fifteen percent variation in energy intensity across the flow path.

In view of the above, I have determined that it would be desirable to have a method and/or apparatus for providing precise measurements of light scatter and fluorescence by accommodating an uneven beam profile of a diode laser.

I have also determined that it would be desirable to have such a method and/or system absent beam shaping optics optically cooperating with or coupled to the laser diode.

I have further determined that it would be desirable to have such a method and/or system including a flow analyzer.

SUMMARY OF THE INVENTION

It is a feature and advantage of the instant invention to provide a method and/or apparatus for providing precise measurements of light scatter and fluorescence by accommodating an uneven beam profile of a light source, such as a laser diode.

It is also a feature and advantage of the instant invention to provide such a method and/or system absent beam shaping optics optically cooperating with or coupled to the laser diode.

It is also a feature and advantage of the instant invention to provide such a method and/or system including a flow analyzer to achieve precise measurements of light scatter and fluorescence emitted by microspheres or beads.

It is a feature and advantage of the instant invention to provide a novel diagnostic system. The instant diagnostic system includes a measurement device including a flow path and a light source, such as a laser diode, and communicatable with a computer. The light source includes a Gaussian first beam profile across the flow path and a second beam profile along the flow path. The diagnostic system further includes a memory medium readable by the computer and storing computer instructions executable by the computer. The instructions include the following sequential, non-sequential, or independent steps. A template relating to a beam profile of the light source is built. A fluorescent sample is captured by the measurement device. The sample is time-wise aligned to the template. The sample is normalized relative to the template. The normalized sample is integrated to determine a total amount of fluorescence in the sample.

Optionally, the template relates to a microsphere size and/or a flow rate. Optionally, the time-wise aligning step includes applying a least squares method for alignment.

Optionally, the measurement device includes a flow analyzer. The flow analyzer is optionally free of a beam profile shaping element optically cooperating with the light source, such as a prismatic expander, a micro lens array, and a beam expander. Optionally, the flow analyzer, in operation, includes a flow path, the beam profile of the light source having a major axis aligned with the flow path. Optionally, the flow analyzer is free of a peak detector for detecting a fluorescence intensity peak for the sample event.

It is also a feature and advantage of the instant invention to provide a computer program product for use with a computer and a measurement device including a light source having a first beam profile and a fluid flow path subject thereto. The computer program product includes a memory medium readable by the computer and storing computer instructions. The instructions include the following sequential, non-sequential, or independent steps. A template relating to the first beam profile of the light source along the flow path is built. The light source includes a Gaussian second beam profile across the flow path. A fluorescent sample is captured by the measurement device. The sample is time-wise aligned to the template. The sample is normalized relative to the template. The normalized sample is integrated to determine a total amount of fluorescence in the sample.

Optionally, the template relates to a microsphere size and/or a flow rate. Optionally, the time-wise aligning step includes applying a least squares method for alignment.

It is another feature and advantage of the instant invention to provide a method of improving a beam profile of a light source, such as a laser diode, in a measurement device. The measurement device includes a flow path and a light source having a Gaussian beam profile across the flow path and a second beam profile along the flow path. The instant method includes the following sequential, non-sequential, or independent steps. A template relating to a beam profile of the light source is built. A fluorescent sample is captured by the measurement device. The sample is time-wise aligned to the template. The sample is normalized relative to the template. The normalized sample is integrated to determine a total amount of fluorescence in the sample.

Optionally, the template relates to a microsphere size and/or a flow rate. Optionally, the time-wise aligning step includes applying a least squares method for alignment.

It is yet another feature and advantage of the instant invention to provide a flow analyzer including a flow cell defining a flow path. The flow analyzer further includes one or more light sources, such as laser diodes, including a Gaussian first beam profile across the flow path and a second beam profile along the flow path. Optionally, the flow analyzer is free of a beam shaping optical element or assembly optically cooperating with one or more of the light sources.

Optionally, the flow analyzer is free of a peak detector for detecting a fluorescence intensity peak of a sample event. Optionally, the flow analyzer further includes one or more optical detectors cooperating with the one or more laser diodes and the flow cell. The one or more optical detectors include an avalanche photodiode, a photomultiplier tube, or a p-i-n photodiode.

Optionally, the flow analyzer further includes one or more analog-to-digital converters communicating with a respective optical detector. The flow analyzer optionally also includes one or more digital signal processor controlling the one or more analog-to-digital converters.

It is another feature and advantage of the instant invention to include, in a flow analyzer including one or more light sources and a flow cell defining a flow path, a method of improving a beam profile characteristic. The method includes orienting the one or more light sources relative to the flow cell so that the one or more light sources includes a Gaussian first beam profile across the flow path and a non-Gaussian second beam profile along the flow path.

Optionally, in the novel method, the flow analyzer is free of a beam shaping element or assembly optically coupled to the one or more light sources. Optionally, the one or more light sources includes one or more laser diodes.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

NOTATIONS AND NOMENCLATURE

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

DETAILED DESCRIPTION OF THE INVENTION

Figure 1:
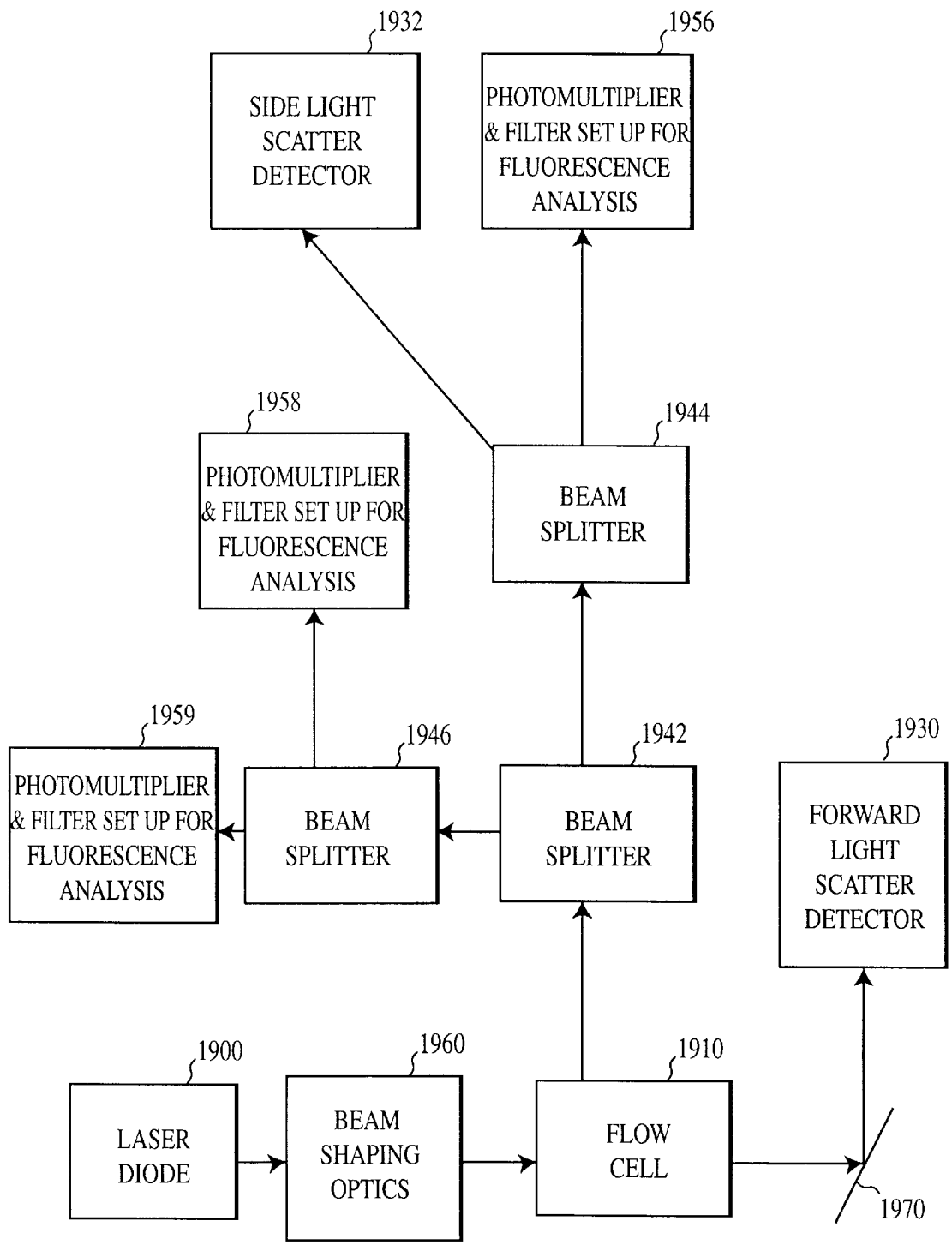
FIG. 1 is a block diagram of a prior art flow cytometer.
Figure 2A:
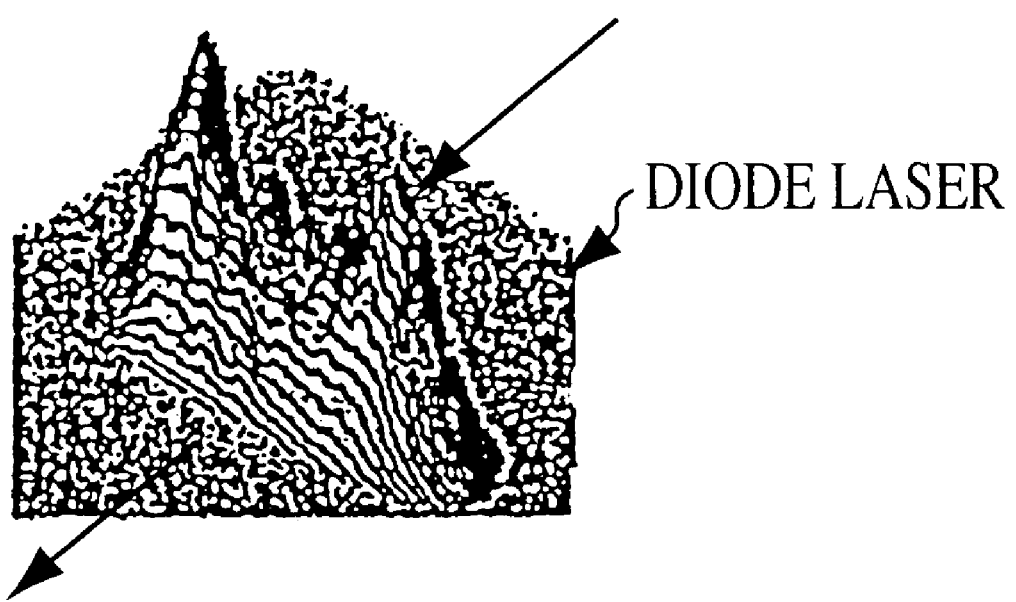
FIG. 2a is a sample Gaussian beam profile of a standard diode laser along a flow path of measurement device as indicated by the arrows.
Figure 2B:
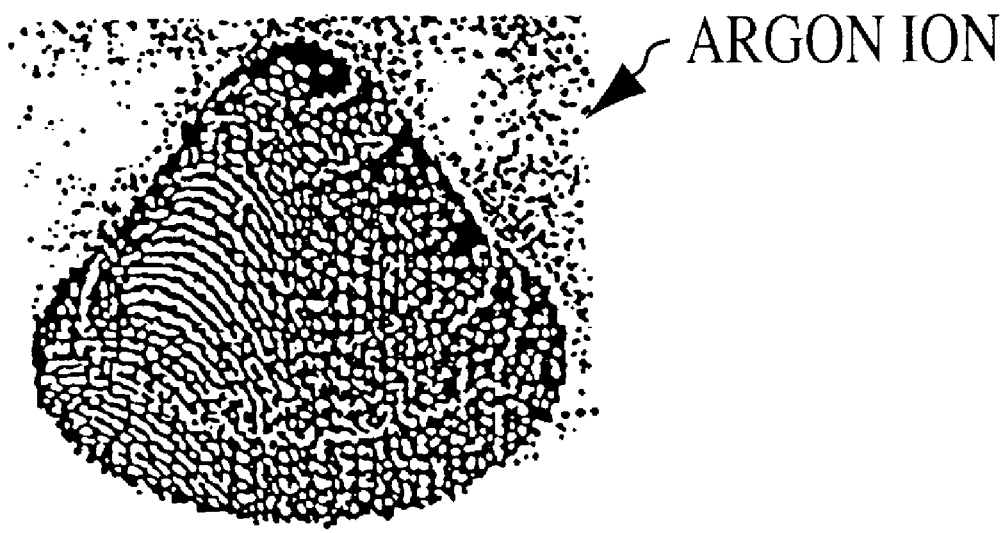
FIG. 2b is a sample beam profile of a standard argon laser.
Figure 3:
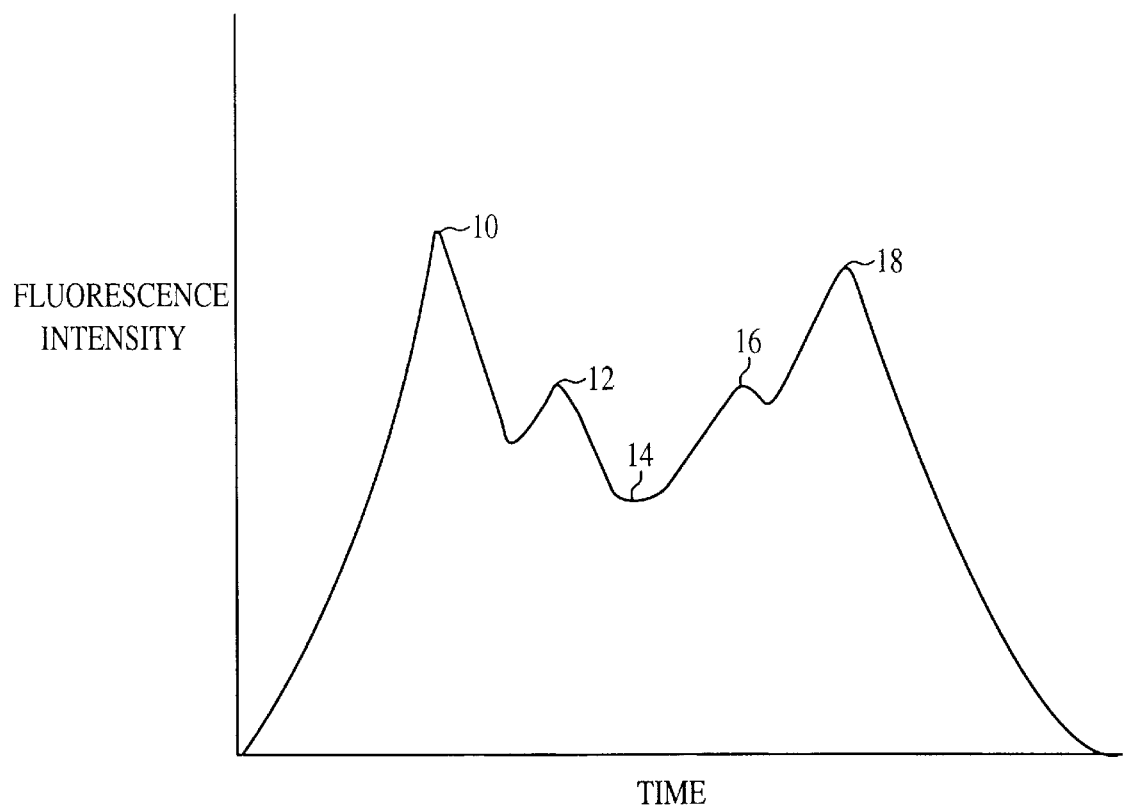
FIG. 3 is a graph of a major axis of a beam profile of a standard diode laser.
Figure 4:
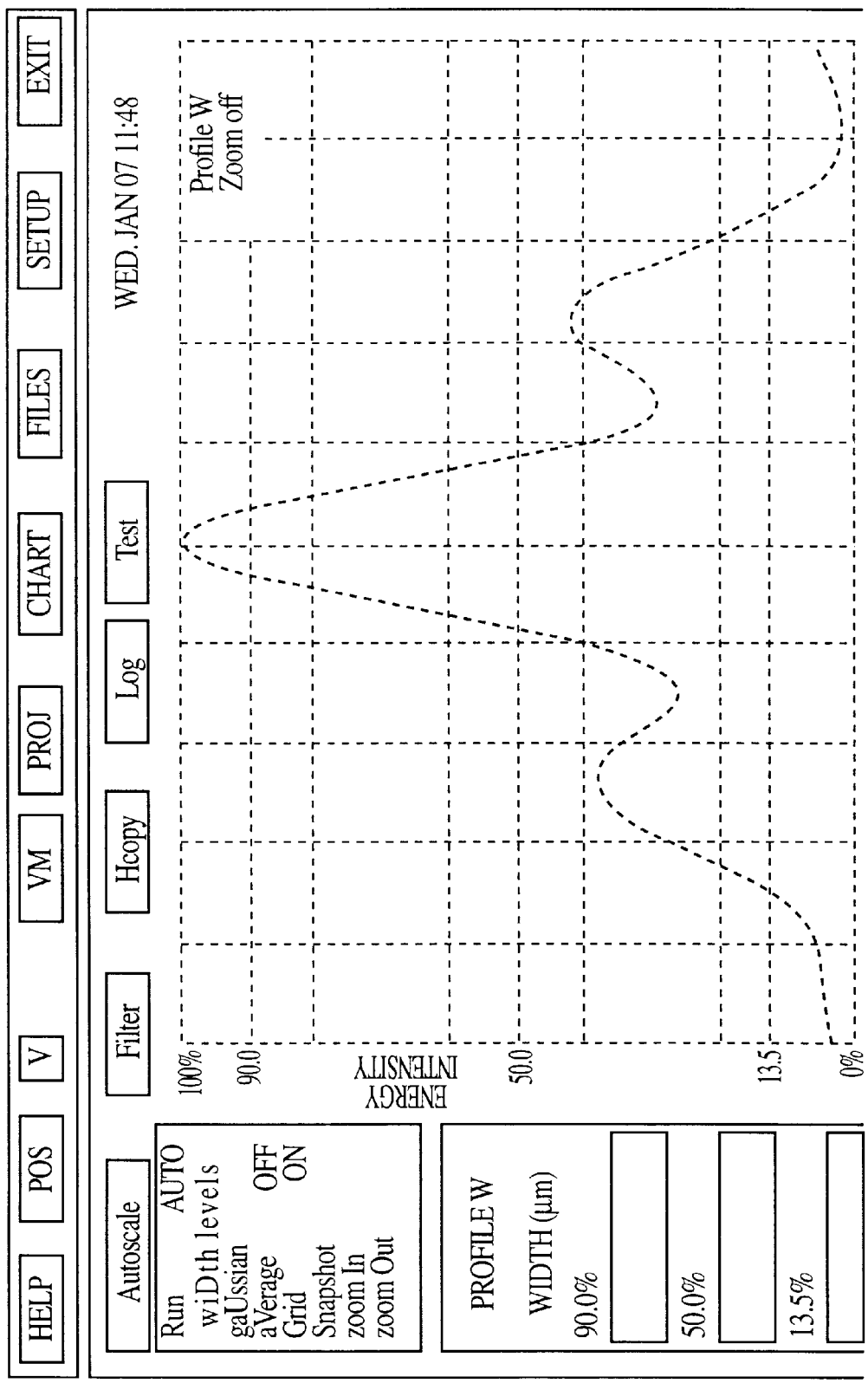
FIG. 4 is a graph of a beam profile of a standard diode laser subject to standard beam shaping optics.
Figure 5:
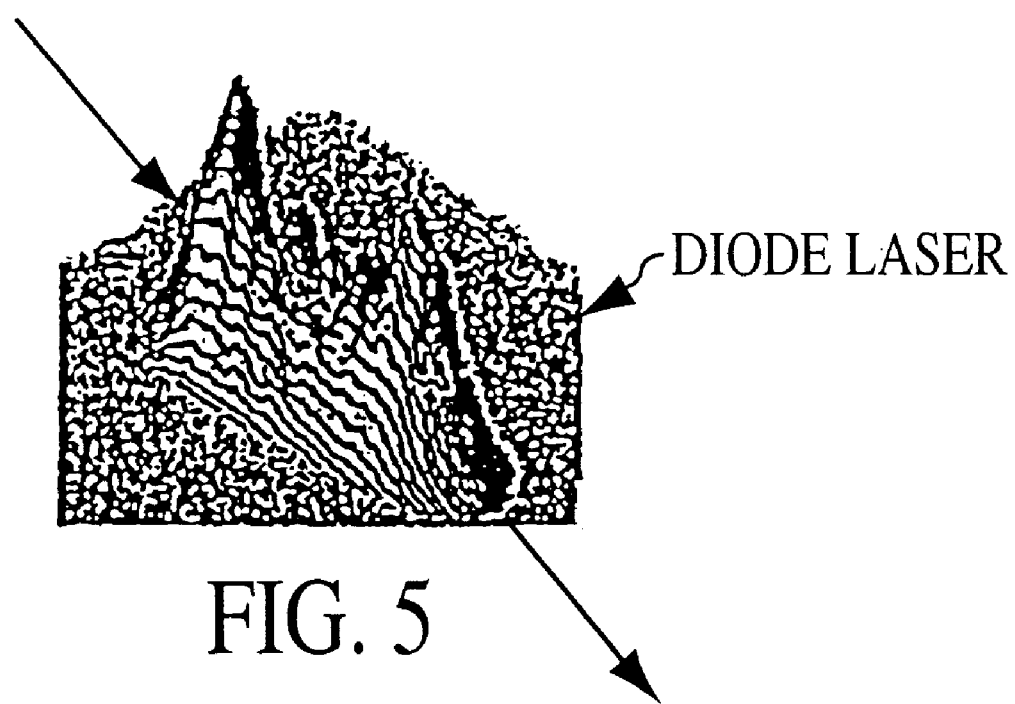
FIG. 5 is a sample beam profile of a standard diode laser across a flow path of measurement device as indicated by the arrows.
Figure 6:
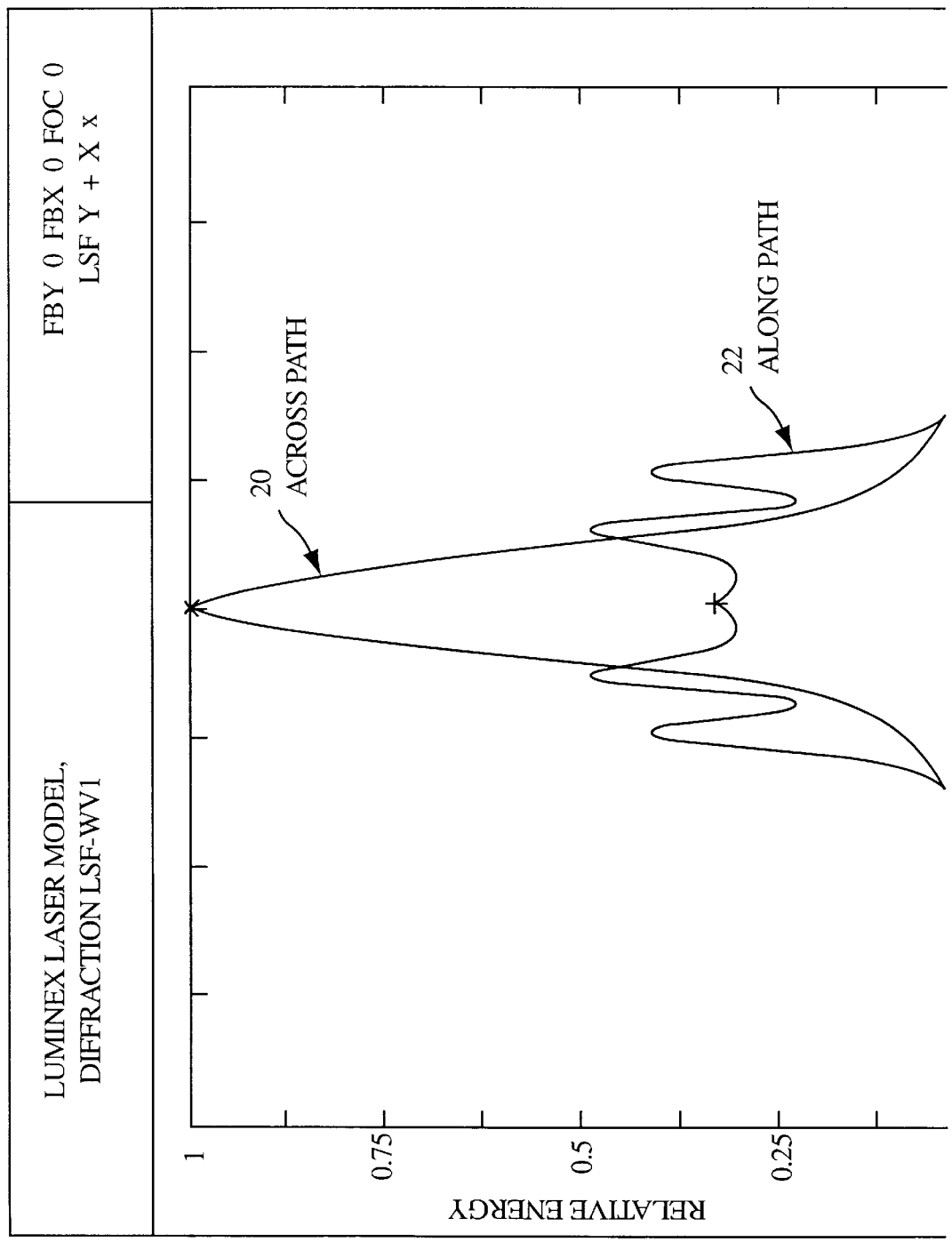
FIG. 6 is a beam profile of a standard diode laser along a flow path superimposed on a beam profile of the same diode laser shifted 90 degrees.

I observed that the beam profile of the diode laser was Gaussian along the flow path of a measurement device with numerous peaks and valleys across the flow path. I positioned the laser diode so as to orient the peaks and valleys portion of the beam profile along the flow path and the Gaussian portion of the beam profile across the flow path, as shown, by way of illustration, in FIG. 5. For completeness, the arrows in FIG. 5 designate the direction of the flow path. For example, to obtain these beam profile orientations, optionally, the laser diode is rotated 90° from an orientation whereby the Gaussian beam profile was along the flow path, as in FIG. 2a. For completeness, the arrows in FIG. 2a designate the direction of the flow path. Unexpectedly and advantageously, the resulting beam exhibited substantially the same off axis performance as the argon ion laser which is Gaussian in both along the flow path and across the flow path. The beam profile of the resulting beam is shown, by way of example, in FIG. 6. Specifically, reference numeral 20 designates the beam profile across the flow path; reference numeral 22 designates the beam profile along the flow path.

Despite the existence of high frequency components, I discovered that substantially uniform standard microspheres used in flow cytometry repeated the complex waveform of beam profile 22 substantially or exactly. I also discovered that the reflection waveform for the beam profile 22 was substantially or exactly the same as the associated fluorescence emission waveform.

Figure 7:
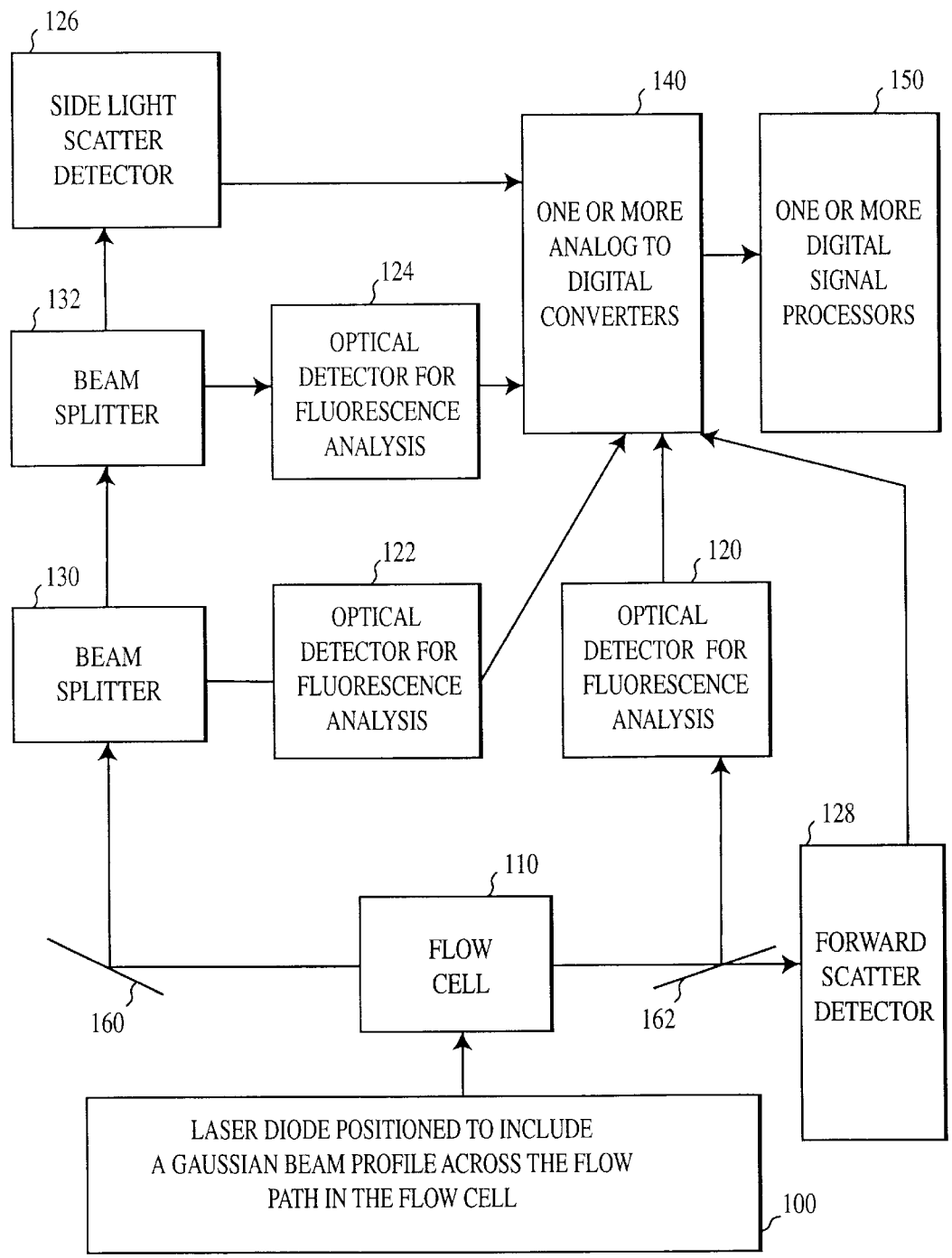
FIG. 7 is a block diagram of an embodiment consistent with the instant invention.

FIG. 7 shows, by way of example, a measurement device consistent with the instant invention. For example, the measurement device includes a standard flow analyzer. A standard laser diode 100 emits a beam, in operation, through a fluid flow stream along a fluid flow path in a standard flow cell 110. The laser diode 100 is positioned so that its beam profile is Gaussian across the flow path of the flow cell 110 and of optionally unknown profile along the flow path. Alternatively, the laser diode is optionally replaced with any standard light source capable of being positioned so that its beam profile is Gaussian across the flow path of the flow cell 110 and of optionally unknown profile along the flow path. Optionally, the measurement device includes any standard instrument having such a light source.

Reflected light and/or fluorescence emissions are detected by one or more standard optical detectors 120, 122, 124, 126, 128. The optical detectors optionally include one or more standard optical detectors 120, 122, 124 for fluorescence analysis. In addition to, or alternatively, the optical detectors optionally include a standard side scatter detector 126 and/or a standard forward scatter detector 128.

The output of the optical detectors 120, 122, 124, 126, 128 are optionally processed by a single standard analog-to-digital converter 140 or a respective analog-to-digital converter for each optical detector. The output of each analog-to-digital converter 140 is input to one or more standard digital signal processors 150 or other standard data processing devices.

The instant measurement device optionally includes one or more standard beam splitters 130, 132, such as standard dichroic mirrors, to direct reflected light and/or fluorescence emissions to one or more of the above-mentioned optical detectors. Optionally, to facilitate miniaturization of the instant measurement device, one or more standard mirrors 160, 162 are advantageously used to direct light to the beam splitters 130, 132 and/or the optical detectors 120, 122, 124, 126, 128.

By way of illustration, the instant invention measures reflected and emitted light with standard optical detectors 120, 122, 124, 126, 128, such as standard avalanche photodiodes (APDs), standard photomultiplier tubes, and standard p-i-n photodiodes. The output of the APDs, for example, is optionally continuously converted to a voltage, which, in turn, is measured by optional analog-to-digital converter 140 under the control of optional digital signal processor (DSP) 150.

Figure 8:
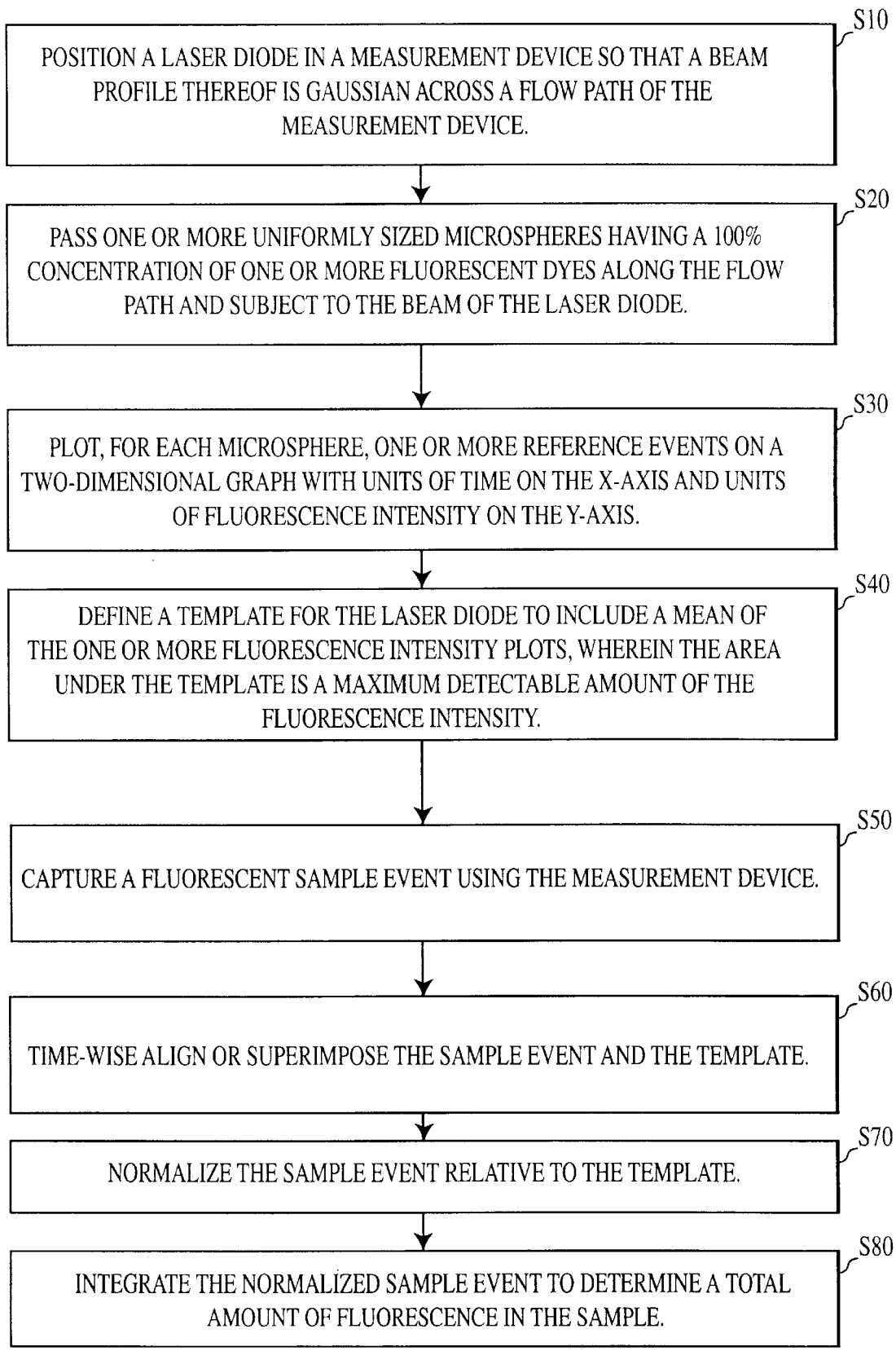
FIG. 8 is a flow chart of a method consistent with the instant invention.

For example, a method of operation of the instant invention is described with reference to FIG. 8. A template relating to the beam profile of a laser diode in a measurement device is built. By way of illustration, an image of the complex waveform representing the laser diode's beam profile along a major axis thereof is stored in the DSP memory as a template. For example, in Step S10, the laser diode 100 is positioned so that a beam profile thereof is Gaussian across a flow path of the measurement device and optionally of unknown profile along the flow path. In Step S20, one or more uniformly sized reference microspheres having a 100% concentration of one or more fluorescent dyes are passed through the flow cell 110 along the flow path and subject to the beam of the laser diode. In Step S30, one or more reference events are plotted, for each microsphere, on a two-dimensional graph with units of time on the X-axis and units of fluorescence intensity on the Y-axis. Plainly, the axes may be reversed. In Step S40, a template for the laser diode 100 is defined to include a mean of a series of time-aligned fluorescence intensity plots of the reference events.

In Step S50, a fluorescent sample event is captured using the measurement device. For example, a microsphere, coated with a reactant specific to an analyte of interest in a biological sample flowing through the flow cell 110, passes through the beam of the laser diode 100. The microsphere includes the same one or more fluorescent dyes used in the reference microspheres. The passing microsphere is sampled at a very high rate, sufficient to record the high frequency components of the complex waveform of the sample event. For completeness, it is to be understood that for each microsphere passing through a beam of the laser diode, one or more sample events are optionally processed therefor, thereby enhancing the accuracy of an assay conducted in accordance with the instant invention. Further, although microspheres have been mentioned above, it is to be understood that any standard fluorophores having, upon excitation, fluorescence emission intensity plots that substantially replicate the beam profile of the light source, for example, a laser diode, are advantageously suitable for use with the instant invention.

In Step S60, the sample event is time-wise aligned to or superimposed on the template. By way of example, a standard least squares fit method is used to time-wise align the event and the template. In Step S70, the sample event is normalized and compared with the template. In Step S80, the normalized sample event is integrated to determine a total amount of fluorescence in the sample. In this manner, by way of example, a microsphere having an 80% concentration of fluorescent dye should yield sample events whereby substantially all points along the time axis have 80% of the fluorescence intensity relative to the template.

Optionally, more than one template is stored for comparisons that represent, for example, different sized beads and/or different flow rates. Optionally, the event is rejected, if there is no good fit between the sample curve and the template. If there is a good fit, the selected template is applied to the other channels. The normalization factor, then, is a linear function of, for example, the scatter and/or fluorescence intensities.

By utilizing this waveform matching technique, I have unexpectedly determined that a flow analyzer can use one or more diode lasers and achieve the same reliable measurements as those given by a $100,000 standard instrument. By way of illustration, there are many applications for this low cost instrument, especially in the field of bead-based assays.

Figure 10:
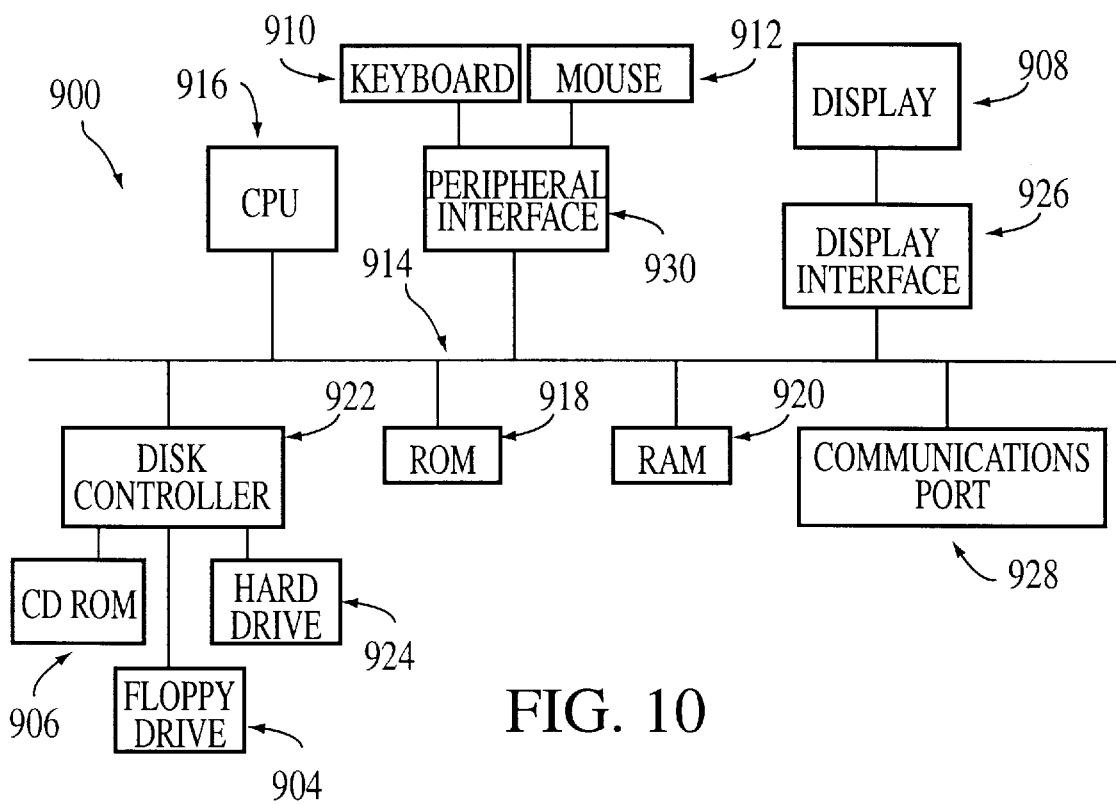
FIG. 10 is an illustrative embodiment of computer architecture consistent with the instant invention.

FIG. 10 is an illustration of a main central processing unit for implementing the computer processing in accordance with a computer implemented embodiment of the present invention. The procedures described herein are presented in terms of program procedures executed on, for example, a computer or network of computers.

Figure 9:
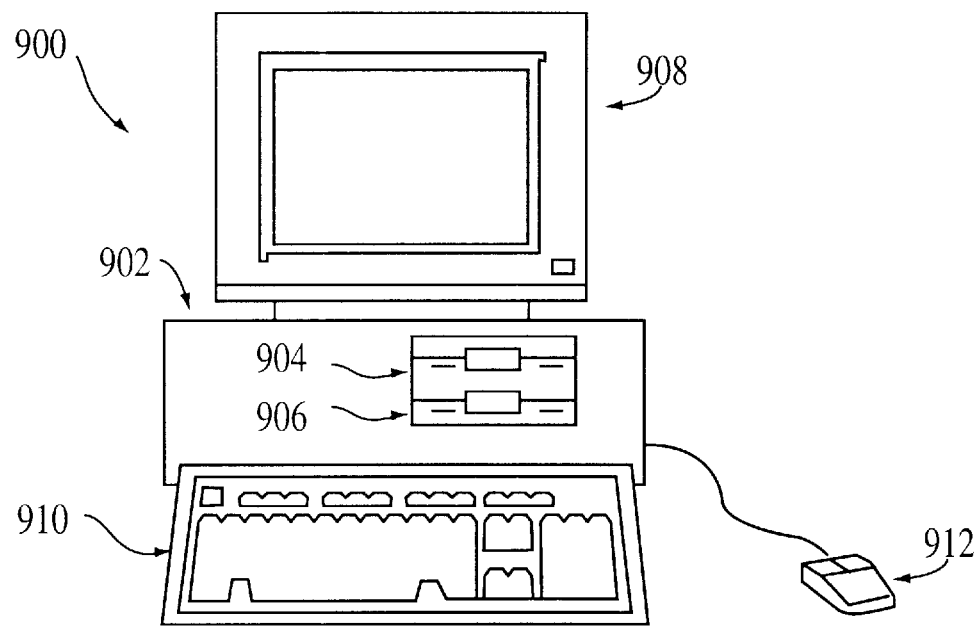
FIG. 9 is an illustrative embodiment of a computer and assorted peripherals.

Viewed externally in FIG. 9, a computer system designated by reference numeral 900 has a computer 902 having disk drives 904 and 906. Disk drive indications 904 and 906 are merely symbolic of a number of disk drives which might be accommodated by the computer system. Typically, these would include a floppy disk drive 904, a hard disk drive (not shown externally) and a CD ROM indicated by slot 906. The number and type of drives varies, typically with different computer configurations. Disk drives 904 and 906 are in fact optional, and for space considerations, are easily omitted from the computer system used in conjunction with the production process/apparatus described herein.

The computer system also has an optional display 908 upon which information is displayed. In some situations, a keyboard 910 and a mouse 902 are provided as input devices to interface with the central processing unit 902. Then again, for enhanced portability, the keyboard 910 is either a limited function keyboard or omitted in its entirety. In addition, mouse 912 optionally is a touch pad control device, or a track ball device, or even omitted in its entirety as well. In addition, the computer system also optionally includes at least one infrared transmitter and/or infrared received for either transmitting and/or receiving infrared signals, as described below.

FIG. 10 illustrates a block diagram of the internal hardware of the computer system 900 of FIG. 9. A bus 914 serves as the main information highway interconnecting the other components of the computer system 900. CPU 916 is the central processing unit of the system, performing calculations and logic operations required to execute a program. Read only memory (ROM) 918 and random access memory (RAM) 920 constitute the main memory of the computer. Disk controller 922 interfaces one or more disk drives to the system bus 914. These disk drives are, for example, floppy disk drives such as 904, or CD ROM or DVD (digital video disks) drive such as 906, or internal or external hard drives 924. As indicated previously, these various disk drives and disk controllers are optional devices.

A display interface 926 interfaces display 908 and permits information from the bus 914 to be displayed on the display 908. Again as indicated, display 908 is also an optional accessory. For example, display 908 could be substituted or omitted. Communications with external devices, for example, the components of the apparatus described herein, occurs utilizing communication port 928. For example, optical fibers and/or electrical cables and/or conductors and/or optical communication (e.g., infrared, and the like) and/or wireless communication (e.g., radio frequency (RF), and the like) can be used as the transport medium between the external devices and communication port 928. Peripheral interface 930 interfaces the keyboard 910 and the mouse 912, permitting input data to be transmitted to the bus 914. In addition to the standard components of the computer, the computer also optionally includes an infrared transmitter and/or infrared receiver. Infrared transmitters are optionally utilized when the computer system is used in conjunction with one or more of the processing components/stations that transmits/receives data via infrared signal transmission. Instead of utilizing an infrared transmitter or infrared receiver, the computer system optionally uses a low power radio transmitter and/or a low power radio receiver. The low power radio transmitter transmits the signal for reception by components of the production process, and receives signals from the components via the low power radio receiver. The low power radio transmitter and/or receiver are standard devices in industry.

Figure 11:
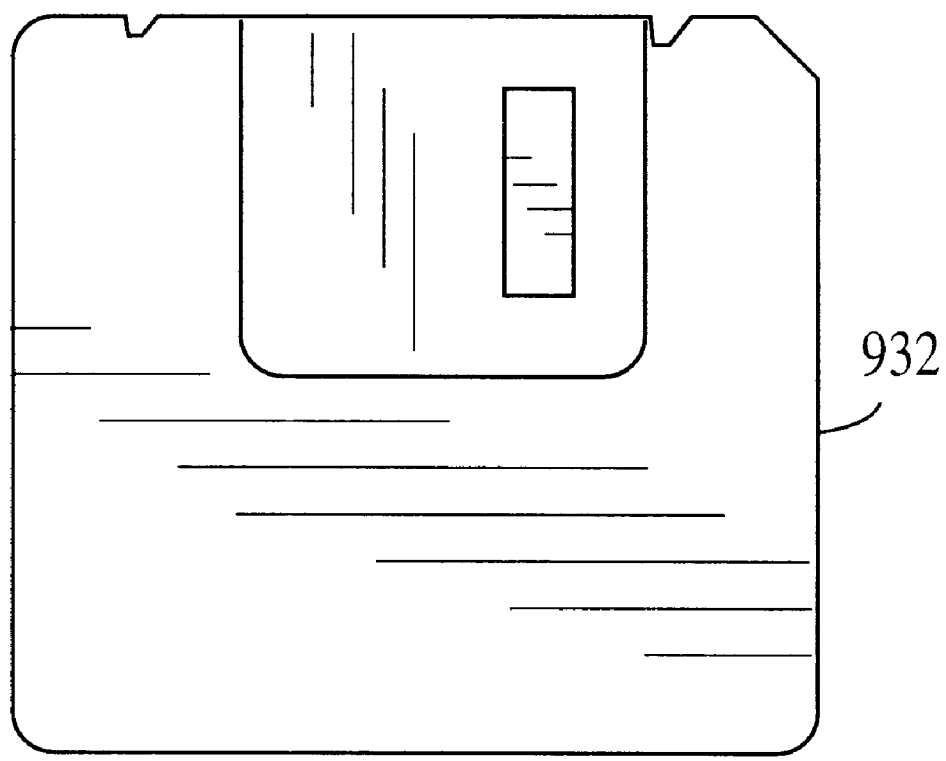
FIG. 11 is an illustrative embodiment of a memory medium.

FIG. 11 is an illustration of an exemplary memory medium 932 which can be used with disk drives illustrated in FIGS. 9 and 10. Typically, memory media such as floppy disks, or a CD ROM, or a digital video disk will contain, for example, a multi-byte locale for a single byte language and the program information for controlling the computer to enable the computer to perform the functions described herein. Alternatively, ROM 918 and/or RAM 920 illustrated in FIGS. 9 and 10 can also be used to store the program information that is used to instruct the central processing unit 916 to perform the operations associated with the production process.

Although computer system 900 is illustrated having a single processor, a single hard disk drive and a single local memory, the system 900 is optionally suitably equipped with any multitude or combination of processors or storage devices. Computer system 900 is, in point of fact, able to be replaced by, or combined with, any suitable processing system operative in accordance with the principles of the present invention, including sophisticated calculators, and hand-held, laptop/notebook, mini, mainframe and super computers, as well as processing system network combinations of the same.

Conventional processing system architecture is more fully discussed in *Computer Organization and Architecture,* by William Stallings, MacMillan Publishing Co. (3rd ed. 1993); conventional processing system network design is more fully discussed in *Data Network Design,* by Darren L. Spohn, McGraw-Hill, Inc. (1993), and conventional data communications is more fully discussed in *Data Communications Principles,* by R. D. Gitlin, J. F. Hayes and S. B. Weinstain, Plenum Press (1992) and in *The Irwin Handbook of Telecommunications,* by James Harry Green, Irwin Professional Publishing (2nd ed. 1992). Each of the foregoing publications is incorporated herein by reference. Alternatively, the hardware configuration is, for example, arranged according to the multiple instruction multiple data (MIMD) multiprocessor format for additional computing efficiency. The details of this form of computer architecture are disclosed in greater detail in, for example, U.S. Pat. No. 5,163,131; Boxer, A., Where Buses Cannot Go, IEEE Spectrum, February 1995, pp. 41–45; and Barroso, L. A. et al., RPM: A Rapid Prototyping Engine for Multiprocessor Systems, IEEE Computer February 1995, pp. 26–34, all of which are incorporated herein by reference.

In alternate preferred embodiments, the above-identified processor, and, in particular, CPU 916, may be replaced by or combined with any other suitable processing circuits, including programmable logic devices, such as PALs (programmable array logic) and PLAs (programmable logic arrays). DSPs (digital signal processors), FPGAs (field programmable gate arrays), ASICs (application specific integrated circuits), VLSIs (very large scale integrated circuits) or the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A diagnostic system comprising:

a measurement device communicatable with a computer and including a flow path and a light source including a Gaussian first beam profile across said flow path and a second beam profile along said flow path; and a memory medium readable by the computer and storing computer instructions executable by the computer, the computer instructions including:

(a) building a template indicative of the second beam profile;

(b) capturing a fluorescent sample event measured by said measurement device;

(c) time-wise aligning the sample event to the template;

(d) normalizing the sample event relative to the template; and (e) integrating the normalized sample event to determine a total amount of fluorescence in the sample event.

2. The diagnostic system according to claim 1, wherein said light source emits a beam, and wherein the template-building instruction comprises passing at least one microsphere, including a substantially one hundred percent concentration of at least one fluorescent dye, through said beam; plotting at least one fluorescent intensity graph for said at least one microsphere; and defining the template to include a mean of the at least one fluorescent intensity graphs, the template including an area therebeneath representing a maximum amount of fluorescent intensity per unit time.

3. The diagnostic system according to claim 1, wherein the template relates to at least one of a microsphere size and a flow rate.

4. The diagnostic system according to claim 1, wherein said time-wise aligning step (c) includes applying a least squares method for alignment.

5. The diagnostic system according to claim 1, wherein said measurement device includes a flow analyzer.

6. The diagnostic system according to claim 5, wherein said flow analyzer is free of a beam profile shaping element optically coupled to said light source.

7. The diagnostic system according to claim 6, wherein said beam profile shaping element includes at least one of a prismatic expander, a micro lens array, and a beam expander.

8. The diagnostic system according to claim 5, wherein said light source includes a laser diode, the beam profile of said laser diode having a major axis aligned with the flow path.

9. The diagnostic system according to claim 5, wherein said flow analyzer is free of a peak detector for detecting a fluorescence intensity peak for the sample event.

10. A computer program product for use with a computer and a measurement device communicatable therewith and including a light source including a first beam profile, and a flow path subject thereto, said computer program product comprising:

a memory medium readable by the computer and storing computer instructions executable by the computer, the computer instructions including:

(a) building a template indicative of the first beam profile along the flow path, the light source including a Gaussian second beam profile across the flow path;

(b) capturing a fluorescent sample event measured by the measurement device;

(c) time-wise aligning the sample event to the template;

(d) normalizing the sample event relative to the template; and (e) integrating the normalized sample event to determine a total amount of fluorescence in the sample.

11. The computer program product according to claim 10, wherein the template-building instruction comprises passing at least one microsphere, including a substantially one hundred percent concentration of at least one fluorescent dye, through the beam; plotting at least one fluorescent intensity graph for the at least one microsphere; and defining the template to include a mean of the at least one fluorescent intensity graphs, the template including an area therebeneath representing a maximum amount of fluorescent intensity per unit time.

12. The diagnostic system according to claim 10, wherein the template relates to at least one of a microsphere size and a flow rate.

13. The computer program product according to claim 10, wherein the time-wise aligning step (c) includes applying a least squares method for alignment.

14. A method of improving a beam profile of a laser diode in a measurement device, the measurement device including a light source including a first beam profile, and a flow path subject thereto, said method comprising:

(a) building a template indicative of the first beam profile along the flow path, the light source including a Gaussian second beam profile across the flow path;

(b) capturing a fluorescent sample event measured by said measurement device;

(c) time-wise aligning the sample event to the template;

(d) normalizing the sample event relative to the template; and (e) integrating the normalized sample event to determine a total amount of fluorescence in the sample event.

15. The method according to claim 14, wherein the template-building instruction comprises passing at least one microsphere, including a substantially one hundred percent concentration of at least one fluorescent dye, through the beam; plotting at least one fluorescent intensity graph for the at least one microsphere; and defining the template to include a mean of the at least one fluorescent intensity graphs, the template including an area therebeneath representing a maximum amount of fluorescent intensity per unit time.

16. The method according to claim 14, wherein the template relates to at least one of a microsphere size and a flow rate.

17. The method according to claim 14, wherein said time-wise aligning step (c) includes applying a least squares method for alignment.

18. The method according to claim 14, wherein the light source includes a laser diode.

19. A flow analyzer comprising:

a flow cell defining a flow path with a sample flowable therethrough;

at least one light source to irradiate the sample and including a Gaussian first beam profile across the flow path and a second beam profile along the flow path.

20. The flow analyzer according to claim 19, wherein said second beam profile includes a non-Gaussian beam profile.

21. The flow analyzer according to claim 19, wherein said flow analyzer is free of a beam shaping optical element or assembly optically coupled to said at least one light source.

22. The flow analyzer according to claim 19, wherein said flow analyzer is free of a peak detector for detecting a fluorescence intensity peak for a sample event.

23. The flow analyzer according to claim 19, further comprising at least one optical detector coupled to said at least one light source and said flow cell.

24. The flow analyzer according to claim 23, wherein said at least one optical detector includes one of an avalanche photodiode, a photomultiplier tube, and a p-i-n photodiode.

25. The flow analyzer according to claim 23, further comprising:

at least one analog-to-digital converter communicating with a respective optical detector; and at least one digital signal processor controlling said at least one analog-to-digital converter.

26. The flow analyzer according to claim 19, wherein said at least one light source includes at least one laser diode.

27. In a flow analyzer including at least one light source and a flow cell defining a flow path, a method of improving a beam profile characteristic, comprising:

orienting the at least one light source relative to the flow cell so that the at least one light source includes a Gaussian first beam profile across the flow path and a non-Gaussian second beam profile along the flow path.

28. The method according to claim 27, wherein the flow analyzer is free of a beam shaping element or assembly optically coupled to the at least one light source.

29. The method according to claim 27, wherein the at least one light source includes at least one laser diode.

* * * * *